(12) United States Patent
Fritz et al.

(10) Patent No.: US 6,770,019 B1
(45) Date of Patent: Aug. 3, 2004

(54) RADIATION SOURCE FOR ENDOVASCULAR RADIATION TREATMENT IN FORM OF A WIRE

(75) Inventors: Eberhard Fritz, Braunschweig (DE); Helmut Menuhr, Braunschweig (DE); Dave Hunt, Didcot (GB)

(73) Assignee: AEA Technology QSA GmbH (DE)

( * ) Notice: Subject to any disclaimer, the term of this patent is extended or adjusted under 35 U.S.C. 154(b) by 12 days.

(21) Appl. No.: 10/088,578

(22) PCT Filed: Sep. 13, 2000

(86) PCT No.: PCT/EP00/08953

§ 371 (c)(1),
(2), (4) Date: Jul. 25, 2002

(87) PCT Pub. No.: WO01/21257

PCT Pub. Date: Mar. 29, 2001

(30) Foreign Application Priority Data

Sep. 20, 1999 (EP) ............................. 99118544

(51) Int. Cl.[7] ................................................. A61N 5/00
(52) U.S. Cl. ......................................................... 600/3
(58) Field of Search ........................................ 600/1–8

(56) References Cited

U.S. PATENT DOCUMENTS 4,994,013 A * 2/1991 Suthanthiran et al. ......... 600/8
5,322,499 A 6/1994 Liprie
5,683,345 A 11/1997 Waksman et al.
5,833,593 A 11/1998 Liprie
6,503,186 B1 * 1/2003 Cutrer ............................ 600/8

FOREIGN PATENT DOCUMENTS

| EP | 0 778 051 A1 | 6/1997 |
| EP | 1 060 764 A1 | 12/2000 |
| EP | 1 060 765 A1 | 12/2000 |
| WO | 97/19706 | 6/1997 |

* cited by examiner

Primary Examiner—Samuel G. Gilbert
(74) Attorney, Agent, or Firm—Pendorf & Cutliff

(57) ABSTRACT

A flexible, radioactive radiation source in the form of a wire or other elongated shape, comprising a matrix of a ductile and/or plastic binder material and a radioactive and/or activatable material. The elastic binder material is preferably a metal, a metal alloy, or a radiation resistant plastic material, or a mixture of these, and the radioactive material, or activatable material once activated, is a β-emitter, a γ-emitter, or an x-ray emitter. The source may be contained, for example, within a tube, capsule, or coating. The flexible, radioactive radiation source may be used for intravascular radiation treatment of cancer, tumor, non-malignant cell growth, scar tissue, or to prevent restenosis.

23 Claims, 3 Drawing Sheets

RADIATION SOURCE FOR ENDOVASCULAR RADIATION TREATMENT IN FORM OF A WIRE

CROSS REFERENCE TO RELATED APPLICATION

This application is a national stage of PCT/EP00/08953 filed Sep. 13, 2000 and based upon EP 99118544.8 filed Sep. 20, 1999 under the International Convention.

BACKGROUND OF THE INVENTION

1. Field of the Invention

The present invention relates to a radiation source for use in endovascular radiation treatment with fission product radioactivity and/or irradiation activated radioactivity, which radiation source is provided in the form of a wire and is suitable for being delivered in a catheter to the selected site to be treated within the vascular system of a patient. The invention further relates to use of said radiation source as well as a method of treatment.

Endovascular radiation treatment is the present method of choice to prevent formation of scar tissue in a blood vessel which has been injured in various ways, for example, as trauma from surgical or diagnostic procedures or for treatment of cancer and tumours. One area of the vascular system of particular concern with respect to such injury relates to coronary arteries that are subjected to procedures for removing or reducing blockages due to plaque within the arteries. Partial and even complete blockage of the coronary arteries by the formation of an arteriosclerotic plaque is well known and a serious medical problem. Such blockages may be treated using arterectomy devices which mechanically remove the plaque, hot or cold lasers which vaporise the plaque, stents which hold the artery open and other devices and procedures well known in the art. The most common of them is the percutaneous transluminal coronary angioplasty (PTCA), more commonly referred to as balloon angioplasty.

2. Description of the Related Art

Long term success of balloon angioplasty procedures is largely limited due to restenosis or re-closing of the intraluminal passageway through the artery by formation of scar tissue. Restenosis is experienced in approximately 30 to 50% of the patients within six months after balloon angioplasty. Apparently, restenosis is to a significant extent a natural healing response to the vessel injury caused by inflation of the angioplasty balloon.

Prior attempts to inhibit restenosis have included the use of various light therapies, chemotherapeutical agents, stents, arterectomy devices, hot and cold lasers and so on. The most promising approach to inhibit restenosis after PTCA is the use of endovascular radiation therapy, i.e. the exposure of the potential or actual restenotic site to ionising or radioactive radiation (brachytherapy).

Another important field for radiation treatment is the localised, internal radiation treatment of cancer, tumours and/or non-malignant cell growth. The advantage of a localised radiation treatment is that the healthy tissue surrounding said tumour is exposed to the possibly hazardous radiation to only a very minor extent, since the radiation can be directed specifically to the target region of the tumour.

Although endovascular radiation therapy in general has been applied advantageously, the devices available for delivery of radiation sources and the radiation sources themselves have certain drawbacks which limit their usefulness. Typically, the devices include a catheter, which is directed by way of a guide wire inserted therein to the site of treatment. The catheter is then used to internally direct the radiation source to the site of treatment.

One typical problem encountered with the catheter and/or the radiation source is related to stiffness of the source which is essentially proportional to its length. Thus shorter radiation sources are typically used to allow them to follow the tortuous anatomy of the heart. To irradiate the entire site of the vessel to be treated a so-called "stepping-treatment" is then employed, wherein the radiation source is moved back and forth in the vessel. Since, however, exact positioning is not possible in a constantly moving vessel, irradiation is not precisely controllable in this "stepping-treatment". Thus, long sources are desirable which allow for one-step treatment of the site in its entire length.

For example, U.S. Pat. No. 5,833,593 discloses a flexible source wire which is modified at its treatment end to receive a radioactive element. A plug seals the unmodified section of the source from the lumen of the modified segment or container which contains the radioactive element. Both ends of the source wire are sealed to prevent leakage of radioactivity.

U.S. Pat. No. 5,683,345 discloses an apparatus and a method for brachytherapy. The radiation source used according this document consists of individual treating elements which may be joined together to form a train of treating elements by use of several lengths of high tempered spring wire to prevent the treating elements from becoming too spaced apart while moving through the catheter.

Other typical drawbacks encountered with prior art radiation sources and devices for delivering the same to the site to be treated are related to the duration of exposure, controllability of the radiation exposure (dosage, homogeneity of treatment), the necessity to conduct a "stepping-treatment", or difficulties in completely and controllably retracting the radiation source from the catheter and therefore the risk of undesirable exposure of both the patient and any medical personal "handling" the treatment device.

To solve this problem the European patent application No. 99 111 100.6 discloses a radiation source comprising a deflectable container comprising at least two seeds or radiation emitting elements. The deflectable container joins the relatively short and stiff seeds to form a flexible radiation source. Similarly EP 99 111 099.0 teaches to form a flexible radiation source by directly linking the individual seeds together while still allowing relative movement. Still both radiation sources have the problem that they are limited with respect to miniaturisation in that they either require the container or require providing the linkage between the seeds. The latter radiation source further implies the risk that the linkage between the seeds is interrupted during the treatment. In this case it may be difficult to retract the entire radiation source out of the body to be treated.

Further, in manufacture of the seeds or source there is the constant demand for miniaturisation, since only miniaturisation will provide sufficiently small sources to treat smaller vessels of the patient and thus to successfully allow for cancer or tumour therapy in other anatomical sites.

It is the object of the invention to overcome these and other drawbacks of prior art radiation sources.

SUMMARY OF THE INVENTION

According to the present invention there is provided a radioactive radiation source in form of a wire comprising a matrix of a ductile and/or plastic binder material and a radioactive and/or activatable material.

Preferably, the plastic binder material has a low capture cross-section for the method of activation of the activatable material and/or a low attenuation factor for the emitted radiation. More preferably the ductile and/or plastic binder material is of non-ceramic nature and comprises a metal, a metal alloy or mixtures thereof or a radiation resistant plastic material, preferably a synthetic rubber.

Preferably, the radioactive or then "activated" material is selected from β-emitters, γ-emitters and/or x-ray emitting materials. More preferably the radioactive material is a nuclear fission product or is an activatable material activated by nuclear excitation by particles, preferably neutrons, protons or photons. Most preferably the material has a maximum particle energy of β-radiation of at least 500 keV, or a photon energy of γ- and/or x-ray radiation in the range of 20 to 100 keV. In a preferred embodiment this radioactive and/or activated material is selected from Sr/Y-90, Tm-170, Si/P-32, P-32, Cl-36, Zn-123, Ce-144, Tb-160,Ta-182, Tl-204, W/Rh-188, Ir-192 and Se-75 or mixtures thereof.

The radioactive and/or activatable material is preferably used in elemental form and/or in form of a compound insoluble under the prevailing compositions, preferably in form of an oxide, fluoride, titanate, carbonate, cermet or ceramic.

The radiation source of the present invention generally has a ratio of length to diameter of $\geq 2:1$, a length in the range of less than 1 to 25 mm and a diameter in the range of 0.01 to 1 mm.

The radiation source of the invention may further comprise a means for containment which is preferably a capsule or a coating.

The radiation source of the invention can be used for radiation treatment of a mammal, preferably a human being. Preferably the radiation source of the invention is used in brachytherapy, preferably endovascular brachytherapy, to treat restenosis, cancer, tumours and non-malignant cell growth or scar tissues.

The present invention makes possible the objects of (1) providing a radiation source having increased mechanical stability at sufficient flexibility of the source to follow the bends of a small vessel, of (2) providing improved security in view of leakage of radioactive material in case the source is damaged or otherwise manipulated during manufacture thereof e.g. by cutting or forming the same, of (3) providing a considerable simplification in manufacture of producing the radiation source, especially when activatable materials are used, and of (4) allowing for miniaturisation of the source in the sub-millimeter region.

DETAILED DESCRIPTION OF THE INVENTION

Figure 1:
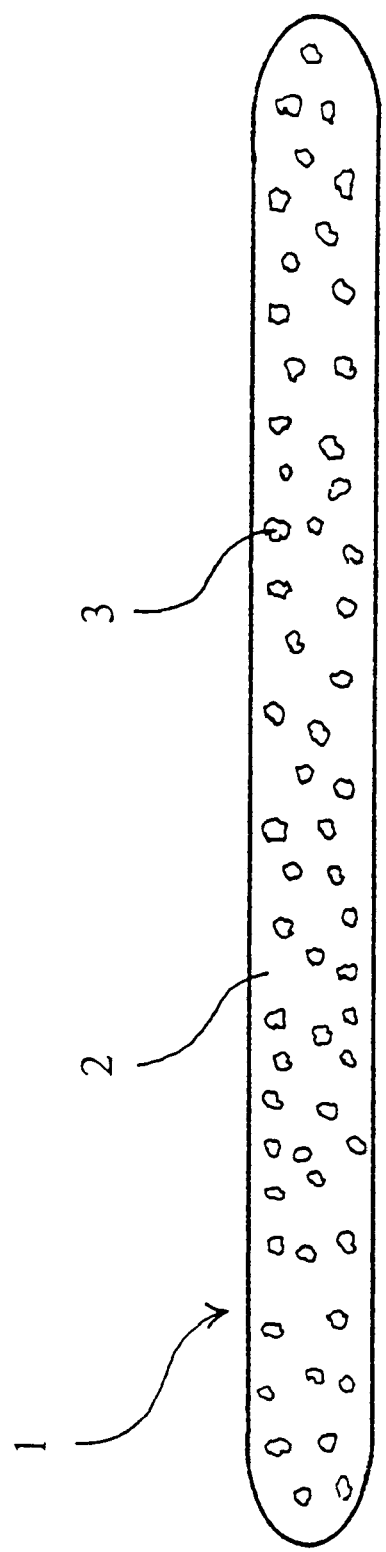
FIG. 1 shows a schematic cross-sectional view of a radiation source of the present invention.
Figure 2:
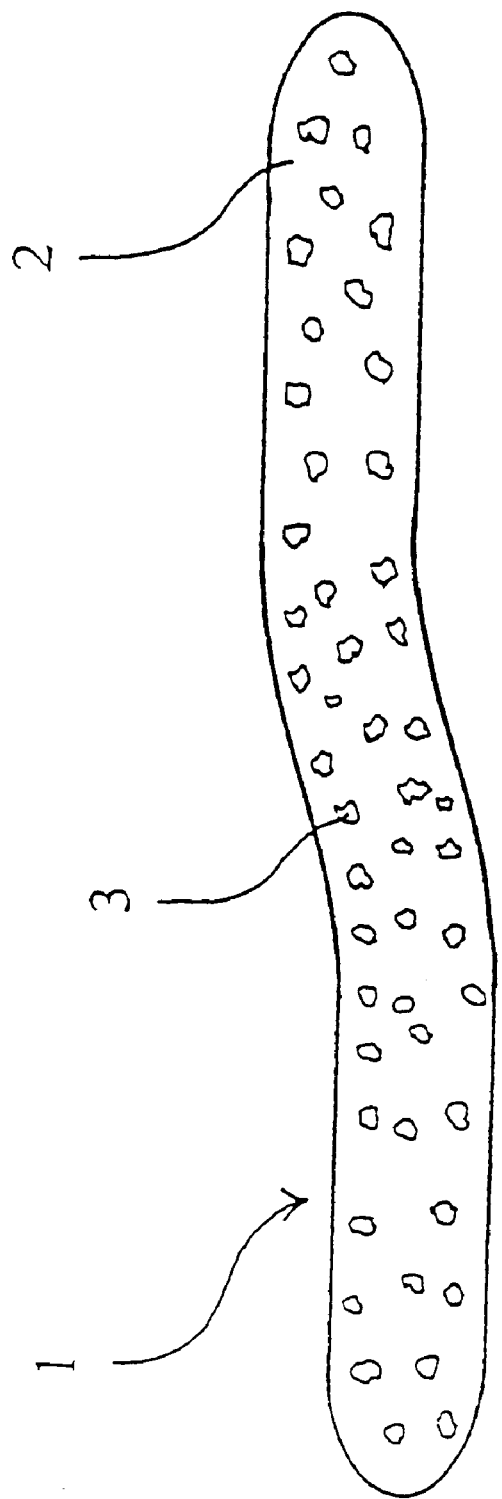
FIG. 2 shows the embodiment of FIG. 1 in a flexed state.
Figure 3:
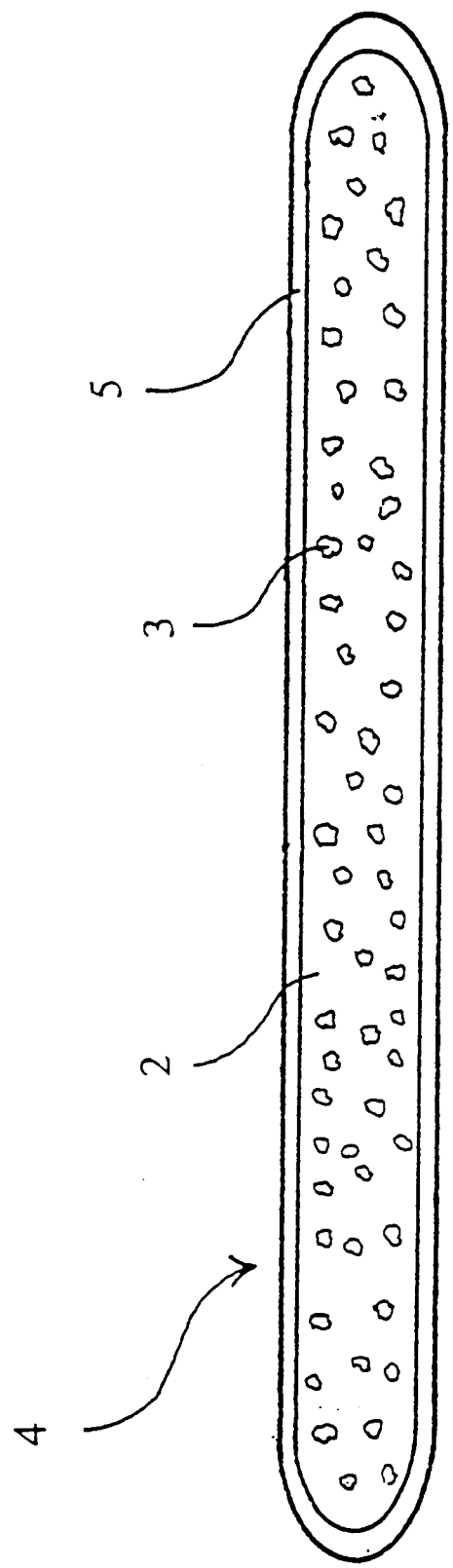
FIG. 3 shows a schematic cross-sectional view of a radiation source of the present invention further comprising a means for containment.

The present invention provides a radioactive radiation source (1) in the form of a wire comprising a matrix (2) of a ductile and/or plastic binder material and a radioactive and/or activatable material (3). Said activatable material can be transformed into an activated material, usually in the form of an isotropically enriched stable isotope, to obtain the activated radiation source to be used in therapy.

The term "wire" as used herein is intended to encompass any form of a radiation source having a ratio of its longitudinal axis (length) to its diameter of $\geq 2:1$. Thus, the radiation source is intended to have an elongated shape. Its cross-section needs not necessarily be circular, but may encompass any suitable cross-section such as circular, oval, elliptic, polygonal, preferably quadratic or rectangular, hexagonal, octagonal or an irregular shape, provided this cross-section does not interfere with its use in a catheter and does not hamper advancing the radiation source through a catheter. The term "diameter" therefore refers to any axis normal to the longitudinal axis.

The term "wire" further implies the radiation source having ductile or elastic or flexible properties to allow the radiation source to easily follow the bendings of vessels within the body to be treated. Preferably the plastic binder material used as a matrix is therefore generally a non-ceramic material and comprises a metal, a metal alloy, mixtures thereof or a radiation resistant plastic material.

Generally, the matrix binder material is non-ceramic in nature to avoid the stiffness of this material. All known metals and/or alloys which can be formed to wires can be used as matrix material. Preferably the matrix or binder material has a small capture cross section so that the applied activation irradiation method only activates the activatable and when activated radioactivity emitting material to obtain the desired type of radiation. Another preferred property of the matrix or binder material is a low attenuation factor for the emitted type of radiation. The latter property allows to reduce self-absorption of the radiation source thereby providing a more homogenous or uniform radiation field. The first property reduces the likelihood of activating the binder material of the matrix, which will therefore preferably be non-active.

The binder material used as the matrix further preferably forms radioactive activation nuclides having a short half-live (preferably less than one day), in cases where the binder material is activated by the activation treatment to activate the radiation emitting element at all. More preferably the binder material is not activated during activation of the radiation emitting element.

Examples of the metal to be used as the ductile binder material include metals selected from the group consisting of Al, Ag, Au, Pb, Cd, Ce, Cr, Co, Cu, Fe, Hg, Hf, Bi, In, Mg, Mn, Mo, Nb, Ni, Pd, Pt, Pr, Re, Rh, Sn, Si, Ta, Ti, Tb, Th, V, W, Y, Yb, Zn, Zr or their alloys and mixtures thereof.

The ductile and/or plastic binder material may also comprise a metal alloy selected from the group consisting of aluminium alloys such as Al/Mg, Al/Cu, Al/Cu/Mg, Al/Mg/Si, Al/Cr, Tinal alloy BB, copper alloys such as brass, bronzes, iron alloys such as Fe/Cr, Fe/Ni, Fe/Cr/Ni, Fe/Cr/Al, nickel alloys such as Ni/Ti, Ni/Cr, nitinol, platinum alloys, titanium alloys such as Ti/Al, Ti/Al/V, Ti/Mo, Woods alloy, Inconel, and amalgams.

More preferably, the binder material is one or a mixture of materials selected from the group Ag, Cu, Al, Ti, Ni, the amalgams and Woods alloy. Most preferably the plastic binder material is aluminium or an alloy thereof.

The plastic binder material may also comprise a radiation resistant plastic material selected from synthetic rubbers such as polyethylene, polypropylene, copolymers thereof, silicon rubber or (meth)acrylics or mixtures thereof. The plastic binder material may also comprise a mixture of such radiation resistant plastic material(s) with one or more of the above metals or metal alloys.

The matrix material may be modified by use of magnetic or other magnetisable materials to provide magnetic radiation sources which can e.g. magnetically be linked to a transfer wire used to advance and retract the radiation source within a catheter lumen.

The radiation emitting element or radioactive material can be a β-emitter, γ-emitter and/or an x-ray emitting nuclide. The radiation emitter can be a fission product or can be an irradiation activated activatable radiation emitter. The term "activatable material" means a non-radioactive material, which can be transformed into a radioactive emitter e.g. by particle irradiation. The term "activated material" refers to the material obtained from said activation.

Activatable materials are preferred, since the radiation source of the invention can be formed by routine steps without requiring appropriate equipment to shield the manufacturing personal and equipment from radiation. The final radiation source is then activated for example by excitation of an activatable material or nucleus by bombardment with charged and uncharged particles, preferably neutrons, protons or photons. Preferred activatable materials are materials activatable by the above nuclear reactions. More preferably these materials have a maximum particle energy of beta radiation of at least 500 keV and a photon energy for γ-radiation and/or x-ray radiation between 20 keV and 100 keV. These radioactive materials are soft emitters which are most desirably used in treatment of biologic materials due to their short attenuation distance, more in detail these materials are desirably due to their local ionizing effect and thus localized biological/medical effect.

By choice of the above emitters, the probability for emission of γ-energies greater than 100 keV is preferably reduced to a better tolerable degree. By use of these preferred 62-emitters and/or γ-emitters and x-ray nuclides the necessary amount of radiation can further easily be introduced into the radiation source of the invention in form of a wire even in case this wire has very small dimensions in the sub-millimeter region.

In a preferred embodiment the radioactive (fission product) or activated material is selected from the group consisting of Sr/Y-90, Tm-170, Si/P-32, P-32, Cl-36, Zn-123, Ce-144, Tb-160, Ta-182, Tl-204, and W/Rh-188, Ir-192 and Se-75 or mixtures thereof. More preferably, the activatable material comprises Tm-170.

In all circumstances the radioactive or activatable/activated material differs from the binder material used as the matrix. Depending on the type of material used, the radioactive and/or activatable material is used in an elemental form and/or in form of a compound insoluble under the prevailing conditions, preferably in form of an oxide, fluoride, titanate, carbonate, cermet or ceramic.

For producing the radiation source of the invention the radioactive and/or activatable material is provided in fine divided form, preferably in form of a powder or granules and is mixed with the binder material of the matrix.

After mixing the wire is formed by conventional techniques to the desired dimensions, e.g. by rolling, casting, forging etc. In case an activatable material is used, the production process to make the radiation source of the invention is simplified as all the fabrication steps to make the wire can be done using the inactive isotope. Namely, there are no radiological dangers to personnel during manufacture and use of the inactive isotope removes the requirement for complex equipment and handling procedures e.g. in enclosed boxes, necessary for the manufacture and processing of radioactive materials.

The radioactive radiation source of the present invention may further comprise (4) a means for containment (5). This means for containment is preferably a sealed capsule preferably in tubular form to contain the wire comprising the matrix and the radioactive material. In another embodiment the means for containment may be a coating which prevents leakage of radioactivity from the wire.

In case of a capsule this is preferably provided in form of a tube sealed on both ends. The capsule may be made from metals or alloys such as steel, preferably stainless steel, V, Ti, Ni, Au, Pt and mixtures and alloys thereof. In case of a coating this may comprise Ni, Cr, Co, Au, Pt, C or mixtures thereof. Such coating may have a thickness of several nm to several 10 μm to prevent leakage of activity. A coating may further be made from radiation resistant plastic materials or mixtures thereof with one of the above materials, if desired.

In general the means for containment is made from a material which has like the binder material of the matrix a small capture cross section for the method used to activate the activatable material and/or has a low attenuation factor for the emitted radiation. Preferably it forms radioactive isotopes or activation nuclides having a short half-life (preferably less than one day), in case the radiation source is activated after manufacture, if it is activated at all.

The amount of radioactivity provided by the radiation source of the present invention is typically in the range of up to 25,000 mCi per centimeter of vessel to be treated, depending on the radioactive and/or activated material used. The emitted radiation should be sufficient to deliver a desired dosage from 100 to about 10.000 rads, preferably about 700 to 5.000 rads in about 2 to 10 minutes to the tissue to be treated.

The radiation source of the invention preferably has a ratio of length to diameter in the range of $\geq 2:1$, preferably 5:1 to 25:1, more preferably 8:1 to 17:1. It further may have a length in the range of less than 1 to 25 mm, preferably 1 to 15 mm, more preferably 2.0 to 10 mm and most preferably 2.5 to 5 mm and may also have a diameter in the range of 0.01 to 1 mm, preferably 0.1 to 0.8 mm, more preferably 0.1 to 0.5 mm and most preferably 0.2 to 0.3 mm.

The radiation source of the invention can be used in intravascular radiation treatment of a mammal, preferably of a human being. More precisely the radiation source of the invention can be used to treat cancer, tumours and other non-malignant cell growth, scar tissue and most preferably to prevent restenosis after balloon angioplasty.

The radiation source of the invention can be used with any known device or apparatus to position the same within the body to be treated. Such apparatus typically comprises a catheter to securely advance the radiation source within the vessels of the body to be treated. The radiation source of the invention can be used as such or can be used as a seed to form a train of radiation emitting elements or seeds. In a preferred embodiment at least two radiation sources of the present invention are used as seeds to form a train of radiation element as disclosed in the European patent applications 99 111 100.6 and 99 111 099.0.

The invention will now be further disclosed by way of specific examples. These examples are given for purpose of illustration only and are not intended to limit the scope of protection.

EXAMPLE 1

Thulium$^{170}$ Wire

The present example refers to a small thulium oxide/aluminium wire as the radiation source.

In the first step naturally occurring $Tm^{169}{}_2O_3$ in form of small particles is mixed with aluminium powder to obtain an evenly distributed mixture of the two materials. The mixing ration of thulium oxide to aluminium is 15 wt % to 85 wt %.

After mixing the material is pressed in and formed according to known procedures into a small wire of approximately 0.3 mm diameter and 2.5 mm length. The wire is fitted into a thin welded pure vanadium capsule which capsule is subsequently sealed to encapsulate the thulium oxide/aluminium wire insert.

The entire capsule is then placed on a nuclear reactor to undergo neutron activation. This creates active $Tm^{170}$ from $Tm^{169}$ and the fabrication process of the source is complete, and a radiation source of 0.4 mm outer diameter and 3.0 mm length can be obtained.

In case pure vanadium is used as the encapsulating material, this capsule like the aluminium as the binder material of the matrix develops no long-living radioactive isotopes during neutron bombardment. Therefore, both the outer encapsulation and the wire binder matrix remain non-radioactive.

EXAMPLE 2

Strontium$^{90}$ Wire

The second example refers to a small strontium fluoride/aluminium wire.

In this case radioactive $Sr^{90}F_2$ in form of a powder is mixed with aluminium powder in an enclosed box. The mixing ratio is 10 wt % $SrF_2$ to 90 wt % Al. The mixture is then pressed and processed to a wire according to known proceedings, although all these proceedings have to be carried out under containment conditions to prevent irradiation of personnel and equipment.

The finally obtained wire has dimensions of 0.5 mm diameter and 2,5 mm length.

According to another embodiment the aluminium matrix was replaced by a copper matrix. In this case, a wire of 0.3 mm diameter and 2.3 mm length was obtained, which was encapsulated in a sealed tube 0.4 mm in diameter and 2.5 mm in length.

Although being described with respect to the preferred embodiments above, this description is not to be considered limiting in that the skilled worker will appreciate the possibility of several variations of the invention as defined in the appending claims, without departing from its scope.

What is claimed is:

1. A radiation source in the form of a wire, wherein said wire comprises a matrix of a ductile binder-material and an elemental or insoluble radioactive and/or activatable material, wherein the radioactive and/or activable material is selected from the group consisting of Sr/Y-90, Tm-170, Si/P-32, P-32, Cl-36, Sn-123, Ce-144, Tb-160, Ta-182, Tl-204, W/Re-188, and Se-75, and mixtures thereof, and the ductile binder-material comprises a metal or a metal alloy.

2. The radiation source of claim 1, wherein the binder-material has a low capture cross-section and is adapted for activation of the activatable material and/or a low attenuation-factor for the emitted radiation.

3. The radiation source of claim 2, wherein the ductile binder-material is selected from the group consisting of Al, Ag, Au, Pb, Cd, Ce, Cr, Co, Cu, Fe, Hg, Hf, Bi, In, Mg, Mn, Mo, Nb, Ni, Pd, Pt, Pr, Re, Rh, Sn, Si, Ta, Ti, Tb, Th, V, W, Y, Yb, Zn, Zr, their alloys and mixtures thereof.

4. The radiation source as in claim 3, wherein said ductile binder-material is Ag, Cu, Al, Ti, Ni, amalgams or Woods alloy.

5. The radiation source of claim 3, wherein the ductile binder-material comprises a metal alloy selected from the group consisting of aluminium alloys, copper alloys, iron alloys, nickel alloys, platinum. alloys, titanium alloys, and amalgams.

6. The radiation source of claim 3, wherein the ductile binder-material comprises a metal alloy selected from the group consisting of Al/Mg, Al/Cu, Al/Cu/Mg, Al/Mg/Si, Al/Cr, Tinal alloy BB, brass, bronzes, Fe/Cr, Fe/Ni, Fe/Cr/Ni, Fe/Cr/Al, Ni/Ti, Ni/Cr, nitinol, Ti/Al, Ti/Al/V, Ti/Mo, Woods alloy, Inconel, and amalgams.

7. The radiation source of claim 1, wherein the radioactive and/or activatable material is used in the form of an oxide, fluoride, titanate, carbonate, cermet or a ceramic.

8. The radiation source of claim 1, having a ratio of length to diameter in the range of >2:1.

9. The radiation source of claim 1, having a ratio of length to diameter in the range of 5:1 to 25:1.

10. The radiation source of claim 1, having a ratio of length to diameter in the range of 8:1 to 17:1.

11. The radiation source of claim 1, having a length of less than 25 mm.

12. The radiation source of claim 1, having a length in the range of 1 to 15 mm.

13. The radiation source of claim 1, having a length in the range of 2.0 to 10 mm.

14. The radiation source of claim 1, having a length in the range of 2.5 to 5 mm.

15. The radiation source of claim 1, having a diameter in the range of 0.01 to 1 mm.

16. The radiation source of claim 1, having a diameter in the range of 0.1 to 0.8 mm.

17. The radiation source of claim 1, having a diameter in the range of 0.1 to 0.5 mm.

18. The radiation source of claim 1, having a diameter in the range of 0.2 to 0.3 mm.

19. The radiation source of claim 1, further comprising a means for containment.

20. The radiation source of claim 19, wherein the means for containment is a capsule or a coating.

21. The radiation source of claim 19, wherein the means for containment is selected from the group consisting of metal, C, a radiation resistant plastic material, and their mixtures.

22. The radiation source of claim 19, wherein the means for containment is selected from the group consisting of Fe, V, Ti, Ni, Au, Pt, Cr, Co and their alloys.

23. The radiation source of claim 1, obtained by a process comprising providing the radioactive and/or activatable material in fine divided form, mixing the same with the binder-material of the matrix, forming the wire by conventional techniques to the desired dimensions, and optionally activating the same.

* * * * *